United States Patent
Fehring et al.

(10) Patent No.: US 6,773,520 B1
(45) Date of Patent: Aug. 10, 2004

(54) ENHANCED BIOCOMPATIBLE IMPLANTS AND ALLOYS

(75) Inventors: Thomas K. Fehring, Charlotte, NC (US); John Harvie Chaffin, III, Concord, NC (US); Richard Lee Kennedy, Monroe, NC (US)

(73) Assignees: University of North Carolina at Charlotte, Charlotte, NC (US); ATI Properties, Inc., Los Angeles, CA (US)

( * ) Notice: Subject to any disclaimer, the term of this patent is extended or adjusted under 35 U.S.C. 154(b) by 0 days.

(21) Appl. No.: 09/660,948

(22) Filed: Sep. 13, 2000

Related U.S. Application Data

(62) Division of application No. 09/247,395, filed on Feb. 10, 1999, now Pat. No. 6,187,045.

(51) Int. Cl.[7] .................................................. C22C 19/07

(52) U.S. Cl. ....................... 148/425; 420/436; 420/437; 420/440

(58) Field of Search ......................................... 420/436

(56) References Cited

U.S. PATENT DOCUMENTS

| | | | |
|---|---|---|---|
| 3,865,585 A | * | 2/1975 | Rademacher |
| 3,871,031 A | | 3/1975 | Boutin |
| 4,012,229 A | * | 3/1977 | Herchenroeder et al. ..... 75/171 |
| 4,491,561 A | * | 1/1985 | Mann .......................... 420/437 |
| 4,530,664 A | * | 7/1985 | Prasad et al. ............... 433/207 |
| 4,668,290 A | | 5/1987 | Wang et al. |
| 4,687,487 A | | 8/1987 | Hintermann |
| 4,714,468 A | | 12/1987 | Wang et al. |
| 4,718,908 A | | 1/1988 | Wigginton et al. |
| 4,822,365 A | | 4/1989 | Walker et al. |
| 4,892,552 A | | 1/1990 | Ainsworth et al. |
| 4,904,262 A | | 2/1990 | Bensmann |
| 5,002,731 A | * | 3/1991 | Crook et al. ................ 420/440 |
| 5,039,574 A | * | 8/1991 | Kulmburg .................... 420/436 |
| 5,152,795 A | | 10/1992 | Sioshansi et al. |
| 5,180,394 A | | 1/1993 | Davidson |
| 5,192,323 A | | 3/1993 | Shetty et al. |
| 5,308,412 A | | 5/1994 | Shetty et al. |
| 5,480,683 A | | 1/1996 | Chabrol et al. |
| 5,507,814 A | | 4/1996 | Gilbert et al. |
| 5,580,352 A | | 12/1996 | Sekel |
| 5,780,119 A | | 7/1998 | Dearnaley et al. |
| 5,891,191 A | * | 4/1999 | Stinson .......................... 623/1 |
| 5,916,518 A | | 6/1999 | Chesnes |
| 6,221,108 B1 | | 4/2001 | Smith |
| 2002/0013625 A1 | | 1/2002 | Abouaf et al. |

FOREIGN PATENT DOCUMENTS

EP  0 897 018 A1  2/1999

OTHER PUBLICATIONS

*Ceramic Bearing Surfaces In Total Artificial Joints: Resistance to Third Body Wear Damage From Bone Cement Particles;* J. R. Cooper et al., Journal of Medical Engineering & Technology, vol. 15, No. 2, Mar./Apr. 1991, pp. 63–67.

(List continued on next page.)

*Primary Examiner*—George Wyszomierski
(74) *Attorney, Agent, or Firm*—Alston & Bird LLP

(57) ABSTRACT

The invention provides improved biocompatible implant alloys and methods of constructing artificial implants having improved long term wear properties. Cobalt-base biocompatible implant alloys provided according to the invention are essentially free of carbide, nitride and sigma second phase particles, and can have hardness and strength properties equivalent to or greater than the standard CoCrMo alloy with significantly improved fatigue life and superior frictional contact properties with UHMWPE. Artificial implant constructions and methods provided according to another aspect of the invention are capable of eliminating latent defects that can promote long term failure of joint implants.

6 Claims, 9 Drawing Sheets

OTHER PUBLICATIONS

*Variables Affecting the Friction and Wear of Metal–on–Plastic Total Hip Joints,* B. L. Gold et al., Metal–on–Plastic Total Hip Joints, No. 100, May 1974, pp. 270–278.

*Modification of the Frictional Surfaces of Artificial Joints,* I. Nishimura et al., Journal of the American Society for Artificial Internal Organs, Inc., Jul.–Sep. 1993, vol. 39, No. 3, pp. M762–M766.

*The Superalloys II,* C. T. Sims et al., John Wiley & Sons, 1987, pp. 135–163.

*Tribology of Artificial Joints,* R. M. Streicher, Morscher E W (ed): Endoprosthetics, Berlin::Springer, 1995, pp. 34–48.

*Femoral Head Technologies to Reduce Polyethylene Wear in Total Hip Arthroplasty,* J. M. Cuckler et al., Clinical Orthopaedics and Related Research, No. 317, 1995, pp. 57–63.

*The Superalloys,* C. T. Sims et al., John Wiley & Sons, 1972, pp. 145–174 and 533–564.

*The Effect of Transfer Film and Surface Roughness on the Wear of Lubricated Ultra–High Molecular Weight Polyethylene,* J. R. Cooper et al., Clinical Materials 14 (1993) pp. 295–302.

*Surface Damage to Cobalt–Chrome Femoral Head Prostheses,* M. Jasty et al., The Journal of Bone and Joint Surgery, vol. 76–B, No. 1, Jan. 1994, pp. 73–77; p. 852.

\* cited by examiner

ENHANCED BIOCOMPATIBLE IMPLANTS AND ALLOYS

CROSS REFERENCE TO RELATED APPLICATIONS

This application is a division of application Serial No. 09/247,395, filed Feb. 10, 1999 now U.S. Pat. No. 6,187, 045, which has been allowed.

FIELD OF THE INVENTION

The invention relates to biocompatible implants and to metal alloys and methods for constructing biocompatible implants. In preferred embodiments, the invention relates to biocompatible joint implants and to materials and methods for constructing these implants.

BACKGROUND OF THE INVENTION

The replacement of joints with man-made artificial joints, i.e., joint arthroplasty, has grown dramatically in the past several decades. Several different joint replacement systems are currently available. However, the worldwide standard remains a cobalt-base superalloy ball structure which fits into a socket formed of ultra-high molecular weight polyethylene (UHMWPE).

The cobalt-base superalloy used in joint implants, CoCrMo, is particularly desirable because of its biocompatibility, high yield strength, and high hardness. American Society for Testing and Materials (ASTM) Specification F 1537 94 defines the chemistry of this alloy as set forth below:

| ASTM F 1537 94 Chemistry | | |
|---|---|---|
| | Min. | Max. |
| C | — | 0.35 |
| Mo | 5.0 | 7.0 |
| Cr | 26.0 | 30.0 |
| Ni | — | 1.0 |
| Fe | — | 0.75 |
| Mn | — | 1.0 |
| Si | — | 1.0 |
| $N_2$ | — | 0.25 |

There is also an ISO specification covering CoCrMo, ISO 5832-12, which is identical in chemistry and very similar otherwise to ASTM F 1537 94.

This alloy is solid solution hardened by the presence of Mo and to some extent Cr, and precipitation hardened by chromium carbides. In addition, the wrought version of the CoCrMo alloy is strengthened by work hardening. This can be accomplished by cold working (e.g. drawing or rolling at room temperature) or by warm working (e.g. rolling at relatively low temperatures within the allowable working temperature range.)

The presence of carbon, in particular, is considered critical to achieve necessary strength properties via the precipitated carbides. Although carbide strengthening is more important for the cast alloy and particularly at elevated temperatures (see Sims, C. T., Stoloff, N. S. and Hagel, W. C., *The Superalloys II*, pp 135–163 (John Wiley & Sons, 1987); nevertheless, even in the wrought alloy which has a relatively low carbon content (typically 0.05%), there are normally huge numbers of very small (<5 μm) carbide particles dispersed throughout the alloy matrix. It is also not unusual to find slightly larger particles of the intermetallic compound, sigma, present in the alloy. Sigma is a very hard and brittle compound of the general formula, $CO_x(Cr, Mo)_y$.

The CoCrMo ball structures used in joint implants are usually machined from wrought bar stock. The thermomechanical forging process reduces the size of the hard carbide particles (as compared to the carbides in cast balls) which increases both alloy strength and hardness, and provides a corresponding reduction in surface roughness of the ball; Streicher, R. M., *Tribology of Artificial Joints*, Endoprosthetics, Morscher, E. W. (Ed.), Berlin:Springer, p. 38–48 (1995). More specifically, the wrought alloy has a fine grain size (ASTM 5 or finer), a high strength (120 Ksi min. Y. S.), and high hardness (Rc35 typical).

Polyethylene wear remains the limiting factor for the longevity of joint arthroplasty. Wear rates on the order of 0.09 mm to 0.3 mm per year have been reported. As a result of such wear, submicron particles are released from the joint at a rate of on the order of 40 billion particles per year.

Whether or not the debris cause an immediate clinical problem depends upon the body's response to the particulate wear debris. Nevertheless, the polyethylene wear particles can have long term effects of bone loss and loosening of the implant. In particular, the wear debris can overload the afferent transport system leading to accumulation of debris around the articulation. A soft tissue membrane forms as a result of the biological reaction to the debris producing soluble factors that stimulate bone resorption, causing osteolysis and loosening of the implant.

The effect of polyethylene wear debris as a primary cause of long term joint implant failure has been known for over two decades and has generated widespread efforts to develop new joint implant structures and materials to reduce wear debris. Substantial effort has been focused on improving the polymers used to form the cup or socket portion of the artificial joint to directly minimize polyethylene debris. Such proposals have included improved sterilization and polymer hardening techniques.

Proposals for improving the ball structure to reduce wear debris in artificial joint implants have focused on frictional properties of the ball surface, and on hardness of the ball alloy. Hardness properties are significant because of third body wear which occurs when particles become trapped between two articulating surfaces. The presence of bone, cement and/or metal debris are believed responsible for roughening of the ball surface in artificial joint implants, causing in turn, increased abrasive, two body wear as the roughened ball grates across the softer polyethylene. Indeed, the tendency of titanium alloy hip prostheses, which were used in the 1970's, to cause rapid polyethylene wear was due to titanium's susceptibility to oxidative and third body wear. This experience led to acceptance of the harder and stronger CoCrMo alloys as the "gold standard", Cukier et al., *Femoral Head Technologies To Reduce Polyethylene Wear In Total Hip Arthroplasty*, Clinical Orthopaedics and Related Research, No. 317, pp. 57–63 (1995).

Despite the high hardness values associated with CoCrMo alloys used in joint implants, scratched and pitted surfaces are also seen in studies of balls of these alloys recovered from patients after use. This has led to proposals for improving surface hardness of the CoCrMo alloy ball. For example, U.S. Pat. No. 5,308,412 to Shetty et al. proposes nitrogen ion implantation to enhance the hardness of the surface of a cobalt-chromium implant. Similarly, Streicher, (cited above), reported improved wear resulting from a TiN coating on cast CoCrMo femoral parts. Alternative ball constructions based on ceramics, particularly zirconia and alumina, have also been investigated because of the extremely high hardness values associated with these materials as disclosed in U.S. Pat. No. 5,180,394 to Davidson; U.S. Pat. No. 3,871,031 to Boutin; and Cooper et al., *Ceramic Bearing Surfaces In Total Artificial Joints: Resistance to Third Body Wear Damage From Bone Cement Particles*, Journal of Medical Engineering and Technology, Vol. 15, No. 2, pp. 63–67 (1991).

Various efforts and proposals have also been made to improve frictional characteristics of the surfaces of artificial implants. As noted previously, the smaller size of hard carbide particles on the surface of the current standard wrought CoCrMo alloy balls provide reduced surface roughness. In particular, reduction in size of the carbides from a diameter of 20 $\mu$m (cast alloy) to 2–3 $\mu$m (wrought alloy) reduced polyethylene wear by 20%, (Streicher, cited above). Gold et al., *Metal-On-Plastic Total Hip Joints*, Clinical Orthopaedics and Related Research, No. 100, pp. 270–278 (1974) suggest a surface roughness less than four micro-inch (0.1 $\mu$m) but greater than 2 micro-inch would be ideal in a metal ball/plastic cup joint implant. Nishimura et al., *Modification Of The Frictional Surfaces Of Artificial Joints*, Journal of the American Society for Artificial Internal Organs, Vol. 39, No. 3, pp. M762–M766 (1993) propose patterned surfaces to improve the frictional characteristics of the articulating surfaces of artificial joints. The pebbled and dimpled patterns can provide reservoirs for lubrication fluids and also provide possible sites for trapping otherwise deleterious wear particles.

Despite numerous studies and research extending over many years, polyethylene wear debris generation in artificial joints remains a significant problem and a substantial cause of long term implant failure. Although numerous modifications and alternatives have been proposed for CoCrMo alloys, the current wrought alloys continue to be the material of choice, particularly for construction of articulating joint surfaces, despite the surface deterioration that occurs over periods of long term use of these alloys.

SUMMARY OF THE INVENTION

The invention provides improved biocompatible implant alloys and methods of constructing artificial implants having improved long term wear properties. Biocompatible implant alloys provided according to the invention can have hardness and strength properties comparable to or greater than the standard CoCrMo alloy, with significantly improved fatigue life and superior wear properties with UHMWPE. Artificial implant constructions and methods provided according to another aspect of the invention are capable of eliminating latent defects that can promote long term failure of joint implants.

According to a first aspect of the invention, artificial implant components are formed of a biocompatible metal alloy having a hardness greater than about 40 Rc, a yield strength greater than about 120 Ksi, and a grain size finer than ASTM 10, and which is essentially free of carbide, nitride, and sigma particles. Preferably, the alloy is an essentially single-phase alloy, i.e., the alloy is essentially free of all second phase particles.

In one advantageous embodiment of the invention, the biocompatible implant alloy is formed of a cobalt-base alloy, preferably a CoCrMo alloy, which is substantially free of carbide, nitride, and sigma second phase particles. In accordance with this aspect of the invention, it has been found that second phase particles can be essentially eliminated in CoCrMo alloys while maintaining biocompatibility, high strength and high hardness values equivalent to or exceeding conventional CoCrMo implant alloys. Moreover, it has been found that elimination of the carbide, nitride and sigma phase particles from CoCrMo alloys can substantially improve the wear properties and fatigue properties of the alloy.

While not wishing to be bound by theory, it has been found that second phase particles on or in the surface of conventional CoCrMo alloy implant structures can detach from, or out of, the alloy surface during accelerated aging in a saline environment, in the complete absence of abrasive contact on the surfaces of the implants. Although the exact cause for separation of the second phase particles is not fully understood, it is believed that separation occurs because the second phase particles have chemical and electrical properties that are different from the remainder of the cobalt-base alloy. In turn, the different electrical and chemical properties of the different portions of the alloy can lead to galvanic corrosion, and/or differential chemical erosion of the alloy surface. Irrespective of the mechanism or cause for detachment of the second phase particles from the main alloys, it is now apparent that these particles are highly susceptible to loosening and removal during the long-term residence time of an implant within the saline and abrasive environment of the body. In turn, the hard second phase particles and the pitted ball surface can generate substantial abrasive wear of a joint implant ball surface, in vivo.

The single phase, high hardness, high strength, biocompatible alloys provided according to the invention are particularly desirable for use in the bearing, i.e., articulating, surfaces of implant components in artificial hip, knee, shoulder, ankle, elbow and other joint implants because they do not generate detached second phase particles, and accordingly minimize third body wear during long term use.

The alloys of the invention are also desirably used to form implant components and fixation structures that are in a juxta-articular position to other implant components, since release of second phase particles may otherwise enhance loosening of implants via various biological responses. In addition, the biocompatible alloys of the invention are also desirably used to form non-articulating implant and fixation devices, and non-articulating components of articulating implant structures. Thus, the alloys of the invention are also desirably used to form various implant stems, base plates and the like, including, for example, acetabular and femoral components of hip replacement implants; tibial and femoral components of knee replacement implants; tibial and femoral stems of knee replacements components of shoulder replacement implants; and non-articulating components of ankle and elbow replacement implants. Similarly, the alloys of the invention are also advantageously used to form fracture fixation devices and components such as nails, screws, and plates.

In general, the substantial absence of second phase particles minimizes the possibility of chemical changes in body fluids and tissues that might result from the electrical and chemical activity associated with in vivo galvanic corrosion, or from the released particles, themselves, during long term use of the implant. Also the improved fatigue strength of preferred alloys of the invention provides longer life and a reduced chance of fatigue failure. Moreover, the improved fatigue properties provide the ability to vary design parameters such as shape and cross-section of implant devices.

In preferred embodiments of the invention, high strength biocompatible alloys essentially free of carbide, nitride and sigma particles are provided having a composition consisting essentially of about 26 to about 28 weight percent chromium, about 5 to about 6 weight percent molybdenum, up to about 1 weight percent manganese, up to about 1 percent nickel, up to about 0.75 weight per iron, up to about 0.07 percent by weight carbon, up to about 0.25 weight percent nitrogen, less than about 0.10% Si, less than about 0.02% Ti, the remainder of the alloy constituting cobalt and impurities. These implant alloys can be provided in a cast or forged form. Preferably, the alloy is in wrought form and has a hardness of about 35 $R_c$, preferably at least about 40 $R_c$, and a yield strength of at least about 120 Ksi, more preferably at least about 130 Ksi. Alloy compositions according to the present invention within these ranges meet all existing chemical requirements of ISO 5832-12 and ASTM F 1537 94. Preferably, the combination of alloy components provided according to the present invention are selected to provide a composition in the form of warm rolled and air cooled bar in which all elements are dissolved within the alloy and there are essentially no second phase particles.

According to a second aspect of the invention, machined artificial implants and implant components of improved long-term wear and durability are provided which are substantially free of latent machining surface defects or damage. In accordance with this aspect of the invention, shaped surfaces of Cobalt-base alloy implants and implant components are prepared using a precision cutting or metal removal operation, which does not leave a thin layer of deformed or damaged material, or otherwise deform the metal alloy.

It has now been found that mirror-smooth surfaces on commercially available balls of femoral implants contain latent, sub-surface scratches, gouges, and rough areas that can be "developed" by exposing the balls to non-abrasive accelerated aging in a saline environment, i.e., accelerated aging in the absence of abrasive contact. More surprising, it has been found that the types and numbers of defects developed during non-abrasive, accelerated aging of unused femoral balls substantially match the defects seen on balls recovered during revision of failed conventional total hip arthroplasties (metal to plastic articulation). It is now believed that the traditional grinding and polishing steps used to prepare articulating implant surfaces generate a polished alloy layer that conceals scratches, and other rough areas formed during an early stage of the manufacturing process. Although various types of subsurface damage of alloy structures by machining operations have been observed before in other technological fields, surface defects on articulating surfaces of alloy implants have been thought due to abrasive contact, in vivo. Despite substantial study and numerous a investigations extending over many years, it has not been previously suggested that conventional grinding and polishing might constitute a substantial cause of surface deterioration, in vivo, of articulating surfaces of cobalt-base alloy implants.

BRIEF DESCRIPTION OF THE DRAWINGS

In the drawings which form a portion of the original disclosure of the invention.

DETAILED DESCRIPTION OF THE PREFERRED EMBODIMENTS

In the following detailed description, various preferred embodiments of the invention are described. It will be understood, however, that the invention is not to be limited to its preferred embodiments. But to the contrary, the invention includes various alternatives and modifications as will be apparent to the skilled artisan from a consideration of the foregoing and from the following detailed description of preferred embodiments of the invention.

BIOCOMPATIBLE SINGLE PHASE IMPLANT ALLOYS

Figure 1:
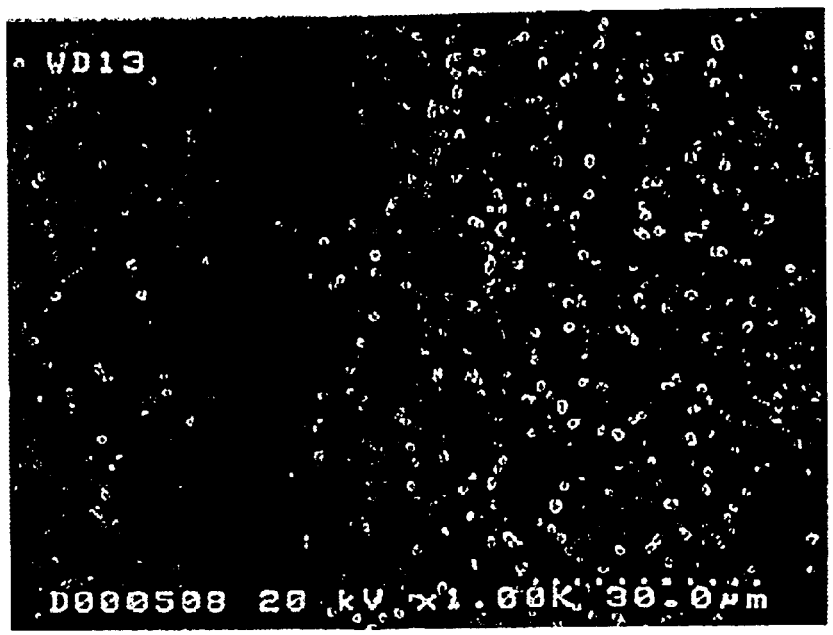
FIG. 1 is a Scanning Electron Microscope micrograph, taken at a magnification of 1000×, of the polished surface of a conventional, prior art, wrought CoCrMo bar stock.
Figure 2:
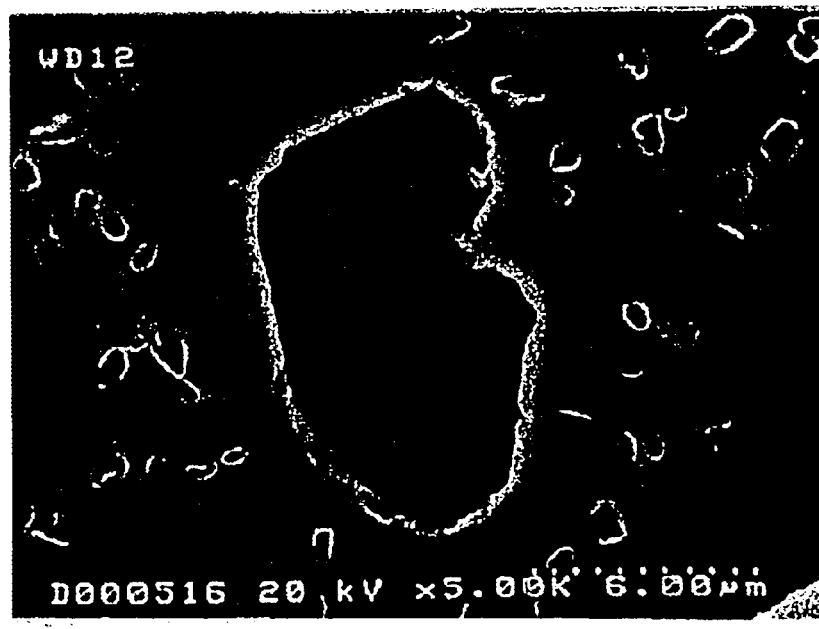
FIG. 2 is a Scanning Electron Microscope micrograph, taken at a magnification of 5000×, of the same wrought CoCrMo bar stock shown in FIG. 1.

FIG. 1 is an SEM micrograph, taken at a magnification of 1000×, of the polished surface of a sample of conventional, prior art, wrought CoCrMo bar stock product prepared according to ASTM Standard F 1537, in the warm worked and air cooled condition, and having a chemical composition typical of wrought CoCrMo alloys used to prepare implant components. FIG. 2 is an SEM micrograph, taken at a magnification of 5000×, of the same wrought CoCrMo bar stock shown in FIG. 1. As seen in FIGS. 1 and 2 this alloy has a microstructure with an extremely large numbers of small second phase particles, which is characteristic of conventional wrought CoCrMo alloys prepared according to ASTM F 1537. The second phase particles have been identified in the literature and by SEM as chromium carbides, $(Cr_xC_y)$, and sigma ($\sigma$) phase intermetallic compounds, $(Co)_x(Cr, Mo)_y$.

Figure 3:
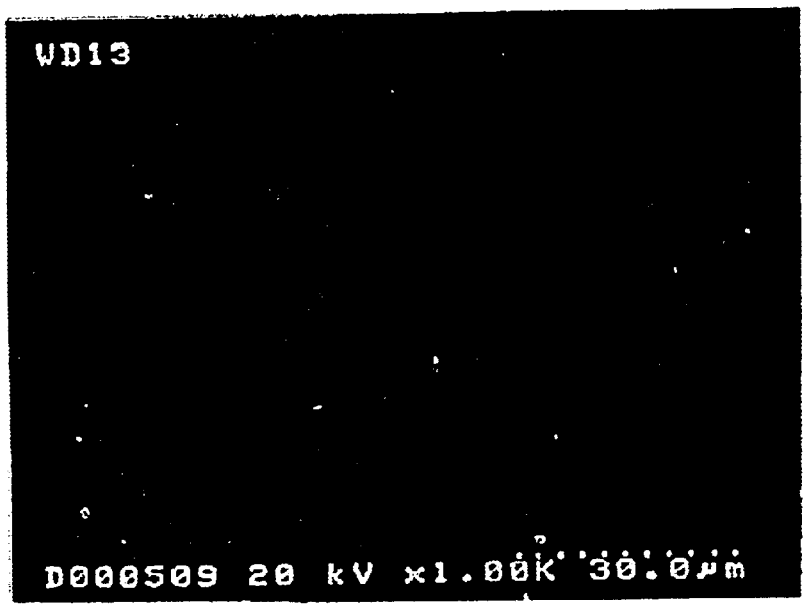
FIG. 3 is a Scanning Electron Microscope micrograph, taken at a magnification of 1000× of the polished surface of a sample of wrought CoCrMo bar stock product according to the present invention.
Figure 4:
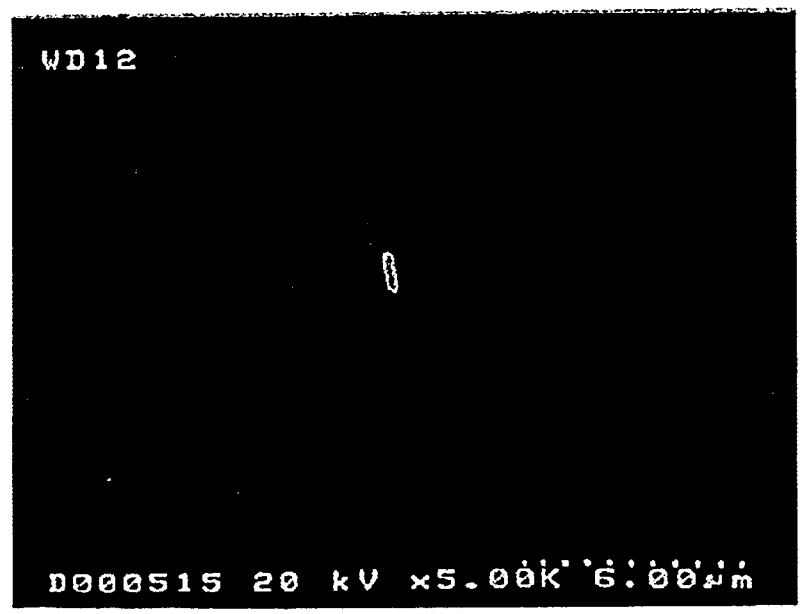
FIG. 4 is a Scanning Electron Microscope micrograph of the same bar stock as shown in FIG. 3, taken at a magnification of 5000×.

FIGS. 3 and 4 are SEM micrographs, taken at magnification of 1000× and 5000×, respectively, of the polished surface of a sample of wrought CoCrMo bar stock product in the identical warm worked and air cooled condition, according to the present invention. As can be seen, this alloy shows a microstructure which is almost completely free of second phase particles, in contrast to the prior art wrought CoCrMo alloys of FIGS. 1 and 2. In addition, the alloy of FIGS. 3 and 4 also meets all requirements of ASTM Standard F 1537, however, the composition of this alloy has been adjusted as compared to the prior art alloys of FIGS. 1 and 2, to maintain the alloy components and compounds thereof within solubility limits.

Although conventional wisdom attributes significant strengthening of CoCrMo alloys to the presence of second phase carbide particles, test samples cut from alloys of the present invention in the warm worked plus air cooled condition and subjected to tensile testing revealed very little difference in tensile properties from prior art alloys (standard commercial practice) as detailed in example 5, despite the almost complete absence of second phase carbide particles in the bar stock of FIGS. 3 and 4. Indeed, the bar stock of FIGS. 3 and 4 exhibits improved wear and fatigue properties as detailed in Examples 4 and 5. Moreover, the absence of carbides and sigma phase particles in this alloy has significant long term wear ramifications for artificial implant structures and components as discussed below.

Figure 5:
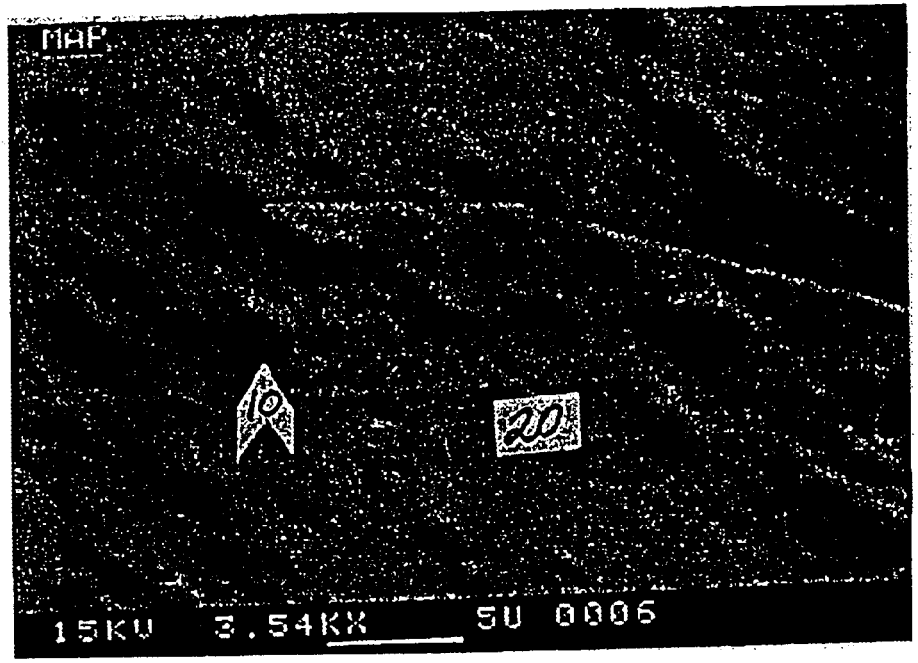
FIG. 5 is a Scanning Electron Microscope (SEM) micrograph, taken at a magnification of 3540×, of a portion of the surface of a commercially available CoCrMo femoral implant ball component, in its virgin, mirror-polished condition.

FIG. 5 is a Scanning Electron Microscope (SEM) micrograph, taken at a magnification of 3540×, of a portion of the surface of a commercially available CoCrMo femoral implant ball component, in its virgin, mirror-polished condition. At this high magnification, a plurality of protrusions, or bumps 10, 1–10 microns in size, are seen extending outwardly of the surface 20 of the implant ball even though the ball surface is highly polished and smooth when evaluated by standard, e.g., precision contact profilometry, procedures. The particular ball surface of FIG. 5 is believed to have a higher density of bumps than most commercially available CoCrMo femoral ball components. However, similar protrusions are believed to be present in varying densities and sizes on all conventional CoCrMo femoral ball components.

Figure 6:
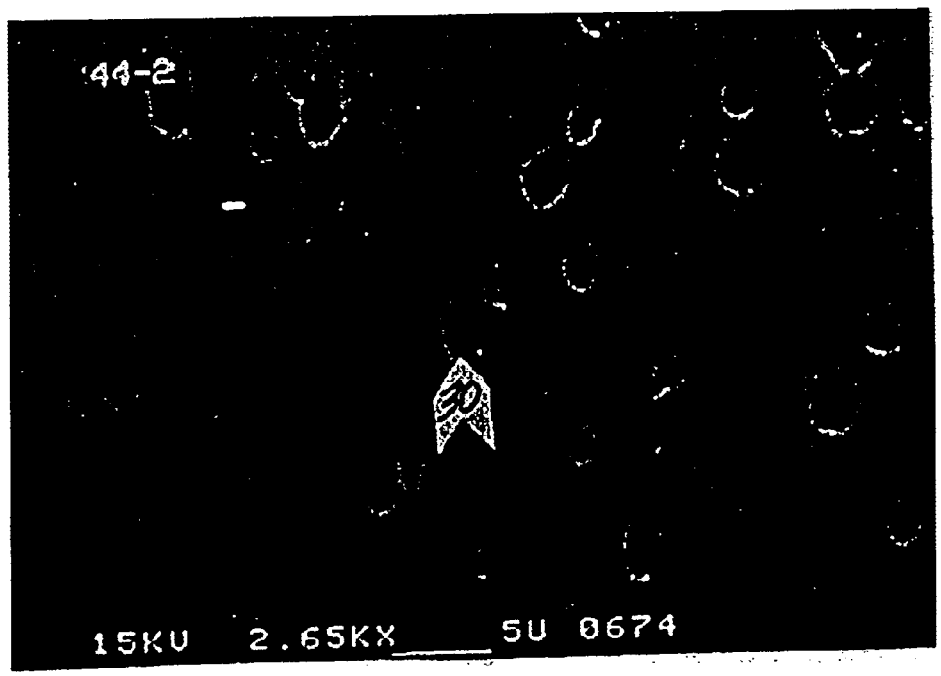
FIG. 6 is an SEM micrograph, taken at a magnification of 2650×, of a portion of the surface of a commercially available CoCrMo femoral implant ball component after treatment by an accelerated chemical aging test.

FIG. 6 is an SEM micrograph, taken at a magnification of 2650×, of a portion of the surface of a commercially available CoCrMo femoral implant ball component after treatment by an accelerated chemical aging test. The accelerated aging test was carried out by immersing the ball in human synovial fluid inside a sealed aluminum pressure vessel, and heating the pressure vessel to a temperature of 159° C., plus or minus 1° C., for 8.6 days. This test is believed to simulate the chemical interactions between the joint synovial fluid and the ball surface that generally corresponds to an in vivo chemical interaction period of 12 years at body temperature, as explained in Example 6. Implant balls traditionally have a flat portion which connects to the implant stem, as is well known to the skilled artisan, and this flat surface rested on the interior bottom surface of the pressure vessel during the test, so that no part of the spherical surface was in contact with any material except synovial fluid. The accelerated aged ball surface of FIG. 6, which is representative of the surfaces of a plurality of commercially available CoCrMo femoral implant balls subjected to accelerated aging, is seen to be distinctly different from the virgin ball surface of FIG. 5. Substantially all bumps have been replaced by angular pits 30, generally less than 5 microns in size and typically in the 1 to 2 micron range.

Analytical testing generally verifies that the pits 30 in the surfaces of accelerated aged balls shown in FIG. 6, result from detachment of the bumps 10 originally present on the virgin ball surfaces of FIG. 5. In particular, examination of the virgin ball surfaces of FIG. 5 by Energy Dispersive x-ray Spectroscopy (EDS), (an elemental analysis procedure for very small portions of a surface to a sub-surface depth of about one micron), revealed an alloy base matrix 20 composed of primarily chromium and cobalt, with small amounts of molybdenum and silicon. In contrast the bumps 10 were strongly enriched in chromium (depleted in cobalt) with about the same amount of molybdenum as the matrix. No silicon was detectable by EDS. Examination by Scanning Auger Microanalysis (SAM), (an elemental surface analysis procedure to a depth of three nanometers) verified the EDS results and also revealed that the bumps 10 contained carbon, in carbide form, and a small amount of oxygen. Neither carbon nor oxygen were found in the alloy matrix 20.

Initial analysis of the pit 30 in FIG. 6 by EDS and SAM showed chromium enrichment and high carbon content as well as a low cobalt content. Subsequently the top layer of the pit was eroded by argon sputtering to determine the chemical profile below the surface of the pit. Following a very brief period of sputtering it was found that the carbon signal diminished to a nominal level, and the cobalt signal increased to a typical level for the matrix of this alloy. Apparently the bottom of the pit 30 included a very thin layer of a chromium-carbon compound (probably chromium carbide), that remained following detachment of a second phase chromium carbide particle from the alloy matrix 20.

Because the accelerated aging test did not replicate any of the mechanical stresses or wear seen by the articulating surface of the femoral implant balls during 10 to 12 years of use, the effects of third body wear or abrasive metallic wear seen by the actual implant in vivo would not be represented due to the non-articular nature of this test. Accordingly the generation of the pits 30 from the bumps 10 must be attributed to chemical interaction.

Although not fully understood, it is believed that the second phase particles are released due to the chemical and/or electrical differences between the second phase particles and the surrounding alloy matrix. For example, contact between different metals in the presence of an electrolytic solution is known to induce galvanic corrosion at the metal interface, e.g., in the area surrounding a second phase particle. Alternatively, it is known that chromium oxide forms on the surface of chromium containing alloys and provides a corrosion-protective film on the base metal. Accordingly, areas which are chromium-lean may have dissolution rates greater than chromium-rich areas leading to non-uniform oxidative degradation. This may occur in alloy areas adjacent chromium carbide, or other second phase particles. As indicated above, the particle itself is rich in chromium while the surrounding area is deplete in chromium. Accelerated dissolution of the metal surrounding the carbide may weaken the alloy matrix surrounding the carbide, so that it eventually breaks off from the matrix leaving a pit.

Irrespective of the mechanism, released carbide, sigma, or other second phase particles can be a source of third body wear, potentially causing damage to the polyethylene joint socket and/or to the femoral head. The irregular pitted surface of the basal matrix can also cause and/or potentiate increased wear. Although wear rates are probably more influenced by peaks than valleys, the irregular nature of these pits probably has some detrimental effect on wear.

Figure 16:
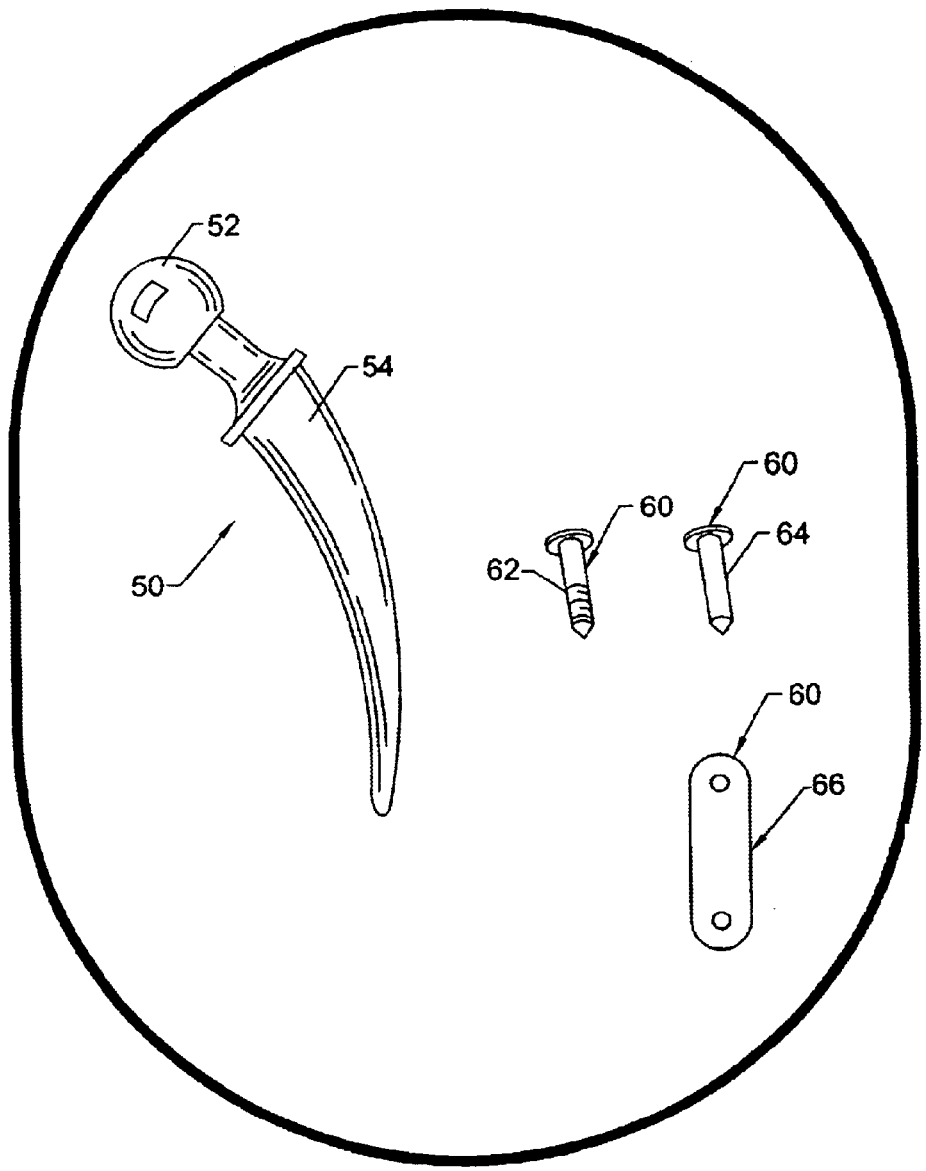
FIG. 16 schematically illustrates a conventional hip implant including a stem component and a ball component and well known fixation devices including a screw, a nail or a pin, and a fixation plate.

Accordingly, artificial implant components according to the present invention are formed of a biocompatible metal alloy substantially free of carbide and sigma second phase particles and preferably essentially free of any second phase particles. The implant and components of the invention are particularly desirable for use in forming articulating implant components in artificial hip, knee, shoulder, ankle, elbow and other joints because they do not generate second phase particles, and/or pitted surfaces. Such articulating components include the ball component 52 of the conventional hip implant 50 illustrated in FIG. 16. In addition, single phase alloys are also desirably used to form non-articulating elements of joint implants such as implant stems and nails, screws, and plates, because of the alloy's improved stability and/or strength. The alloys of the invention are also desirably used to form implant components and fixation structures that are positioned in juxtarticular locations in the body since release of second phase particles may otherwise enhance loosening of implants via various biological responses, and may cause chemical changes in body fluids and tissues. Examples of such components are illustrated in FIG. 16 and include the stem 54 of the hip implant 50, and the fixation devices 60 which include a screw 62, a nail or pin 64, and a fixation plate 66.

A preferred single phase biocompatible implant alloy according to the invention is formed of cobalt-base alloy, preferably a CoCrMo alloy, which is essentially free of carbide and sigma second phase particles. The cobalt-base alloy compositions of the invention are prepared using conventional apparatus and processes known to those skilled in the art. Preferably, the alloy components are melted in a vacuum induction furnace to produce an electrode, which is subsequently remelted by vacuum arc (VAR) or electroslag remelting (ESR) to accomplish refining of the alloy, i.e., reduction or removal of undesirable elements such as $O_2$, removal of volatile elements, plus complete and uniform mixing. The resulting ingot is subsequently thermomechanically processed by a combination of forging, rolling and finishing operations (as will be known to the skilled artisan) to a final bar stock of the appropriate size and mechanical characteristics.

In general, the quantity of carbon present in the composition should be below about 0.07 wt. % in order to prevent the, formation of second phase carbide particles. However, as we have discovered, tie exact limits on carbon will vary depending upon the quantities of other alloying components in the melt. Thus, carbon can be maintained in solution in warm worked and air cooled bar in higher quantities, without the formation of insoluble carbides (in a cobalt-base alloy) when Mo, Cr, and/or Si components are maintained in lower levels in the alloy. This can be seen clearly from Example 1, Table A. In particular, samples prepared from a forged and air cooled bar of heat G917-1 of Example 1 were completely fee of carbides phase. After increasing the Mo, Cr and Si content, while all other elements remain almost unchanged (especially C), heat G917-2 had large amounts of small carbide and larger, blocky sigma phase particles. These differences are clearly shown in FIGS. 1–4.

Preferably, the alloy of the invention comprises a chromium content of from about 26 to about 28 wt. %, and a molybdenum content from about 5 to about 6 wt. %, solubilized carbon is preferably included in the alloy in an amount up to about 0.07 wt. %, less than 0.10 wt. % Si, less than 0.021 wt. % Ti and up to about 1 wt. % nickel, up to about 0.75 wt. % iron, up to about 1 wt. % manganese, with balance Co and incidental impurities.

As discussed previously, cobalt-chromium-molybdenum alloys form a hard intermetallic compound known as sigma phase. In order to avoid formation of insoluble sigma phase materials, the ratio of wt. % cobalt to the sum of wt. % chromium plus one half the wt. % molybdenum is preferably maintained in the range of below about 0.450 max.

Preferably, the alloy composition includes from about 0.10 to about 0.25 weight percent nitrogen which is added as a strengthener. However, it has been found that nitrogen compounds can react to form blocky second phase TiN particles in CoCrMo alloys in the presence of even very small traces of titanium. Although titanium is not usually added as a purposeful component, in order to prevent the formation of undesirable second phase TiN particles, titanium content should be restricted to 0.02 wt. % maximum when nitrogen is added.

Although forging processes will generally tend to improve the structure and improve all mechanical properties, i.e., strength, hardness, fatigue, etc., of the alloy, implant components can be prepared according to the invention from cast alloys where maximum mechanical properties are not required. As discussed previously, the alloys of the invention are essentially free of carbide, nitride and sigma second phase particles and are preferably essentially free of all second phase particles. In this regard, it is to be noted that in general, it is not possible to eliminate all second phase particles from an alloy. Returning briefly to FIGS. 3 and 4, it will be seen that several small particles can be seen in the structure (albeit dramatically fewer than in FIGS. 1 and 2). These particle are aluminum oxides resulting form the Al deoxidizing additions to each heat and/or the melting refractories employed in manufacture. They are separate and apart from the carbides and sigma phase particles observed in FIGS. 1 and 2, and are undoubtedly present in both heats. As used herein, the phrase "essentially free of second phase particles" is intended to include the alloys of FIGS. 3 and 4 and similar alloys in which minute amounts of various incidental, non-uniformly distributed particles can be found in the matrix.

In the most preferred embodiments of the invention, single phase, high strength biocompatible alloys are provided halving a composition consisting essentially of about 26 to about 27 weight percent chromium, about 5 to about 5.5 weight percent molybdenum, up to about 0.8 weight percent without Ni up to about 0.5 weight percent manganese, up to about 0.5 weight percent iron, up to about 0.05 percent by weight carbon, up to about 0.20 weight percent nitrogen, less than about 0.10 weight percent Si, less than about 0.02 weight percent Ti, less than about 0.10 weight percent Al, the remainder of the alloy constituting cobalt and impurities. These implant alloys can be provided in a cast or wrought condition. Preferably, the wrought alloy has a hardness of about 35 $R_c$, more preferably at least about 40 $R_c$, and a yield strength of at least about 120 Ksi, more preferably at least about 130 Ksi. Alloy compositions according to the present invention within these ranges meet all existing chemical and mechanical regulations set forth in ASTM F 1537 94.

Latent Surface Defects

FIGS. 7, 8, 9 and 10 are optical micrographs taken at a magnification of 100× using a Nomarski microscope of femoral balls recovered during revision of failed conventional total hip arthroplasties (metal to plastic articulation) and illustrate pits, scratches, gouges, and rough patches developed on CoCrMo balls during long term in vivo use. In each case, the femoral balls had been used for a period exceeding ten years.

FIGS. 11, 12, 13 and 14 are optical micrographs, each taken at a magnification of 100× using a Nomarski microscope, of a commercially available CoCrMo femoral implant ball component after treatment using the accelerated chemical aging test discussed previously in connection with FIG. 6 and described in greater detail in Example 6. Even though the balls shown in these figures had nearly flawless surfaces prior to accelerated aging, and even though no abrasive contact was applied to the articulating ball surface during accelerated aging, the defects shown in FIGS. 11–15 were developed during aging. These defects are strikingly similar to the defects on used femoral balls as shown in FIGS. 7–10.

Figure 7:
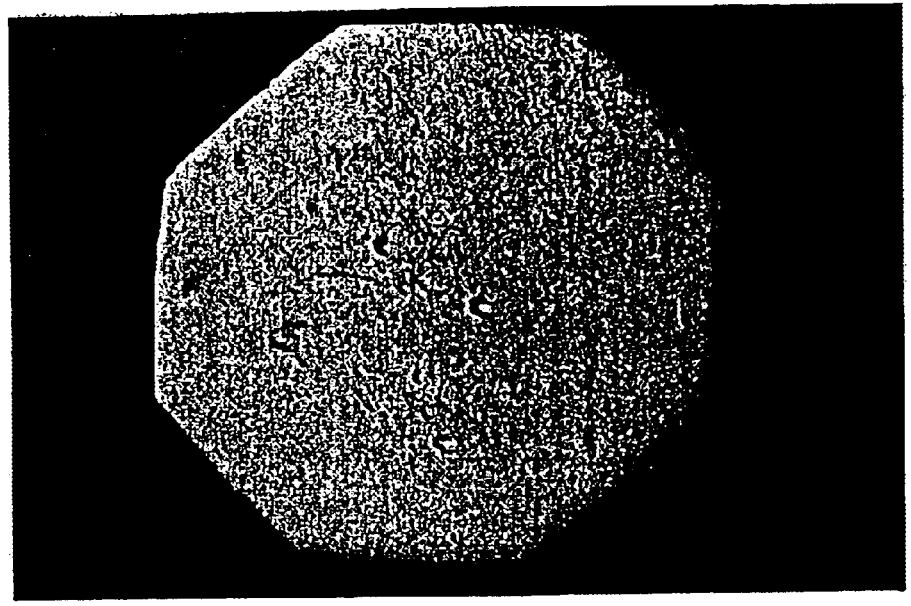
FIGS. 7, 8, 9 and 10 are optical micrographs, each taken at a magnification of 100× using a Nomarski microscope, of CoCrMo alloy femoral balls recovered during revision of failed conventional total hip arthroplasties, and respectively illustrate pits, scratches, gouges, and rough patches developed during long term in vitro use.
Figure 8:
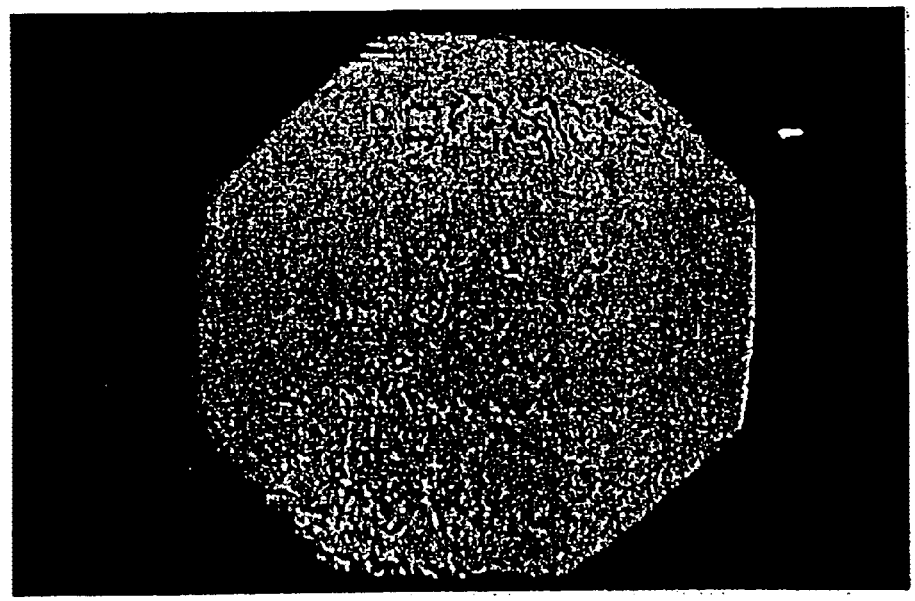
Figure 9:
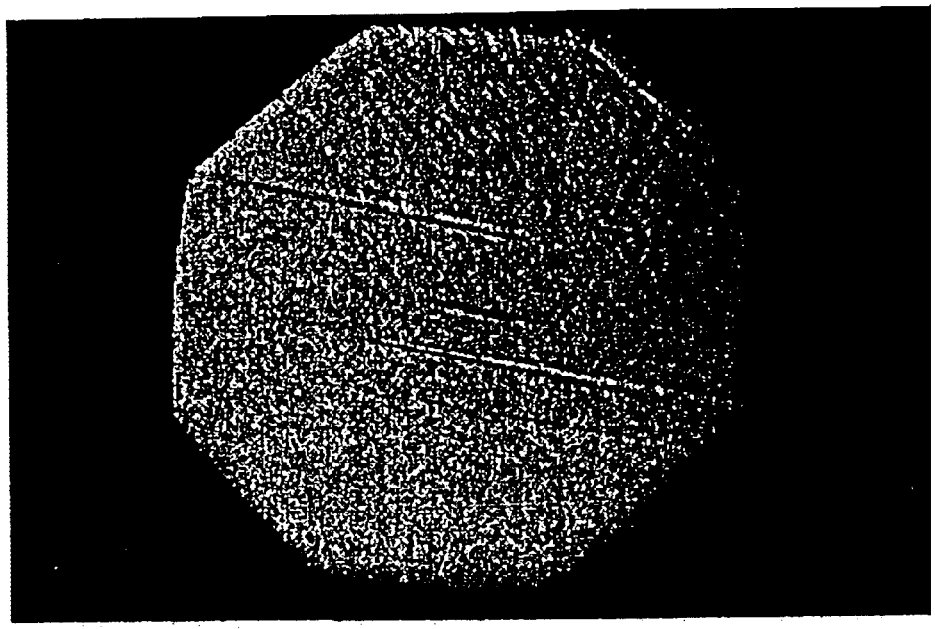
Figure 10:
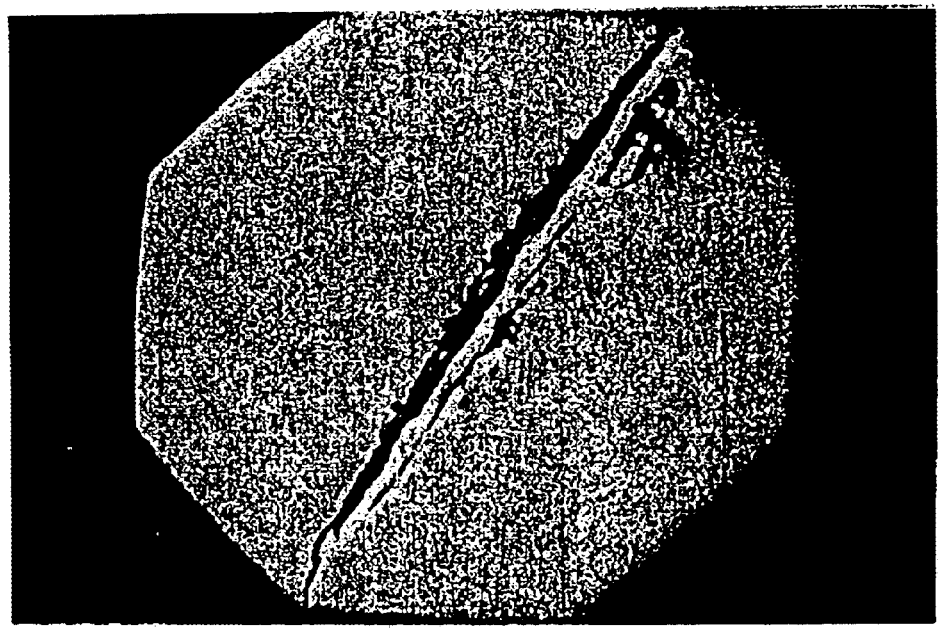
Figure 11:
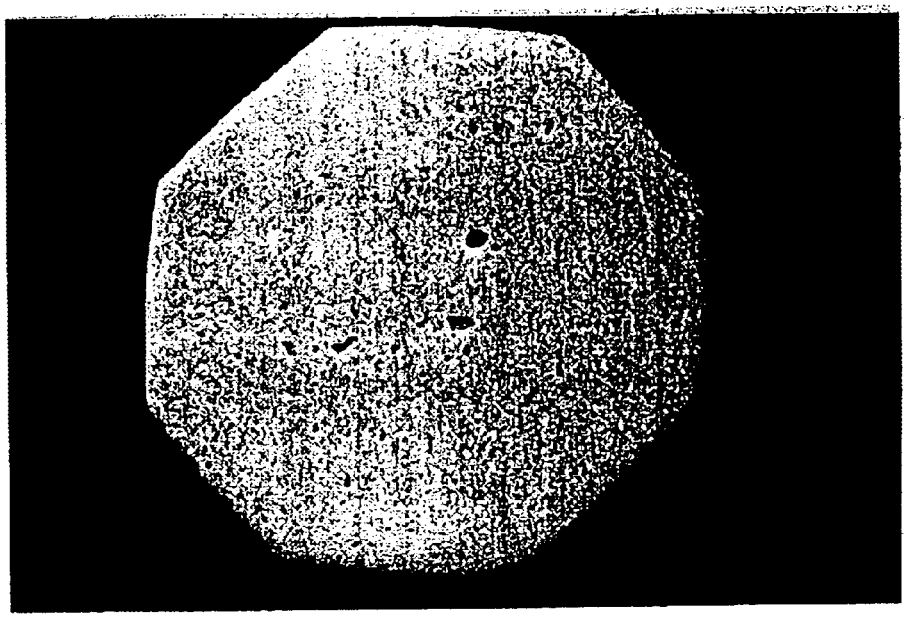
FIGS. 11, 12, 13 and 14 are optical micrographs, each taken at a magnification of 100× using a Nomarski microscope, of a commercially available CoCrMo femoral implant ball component after non-contact accelerated chemical aging, conducted in human synovial fluid for 8.6 days at 159° C.
Figure 12:
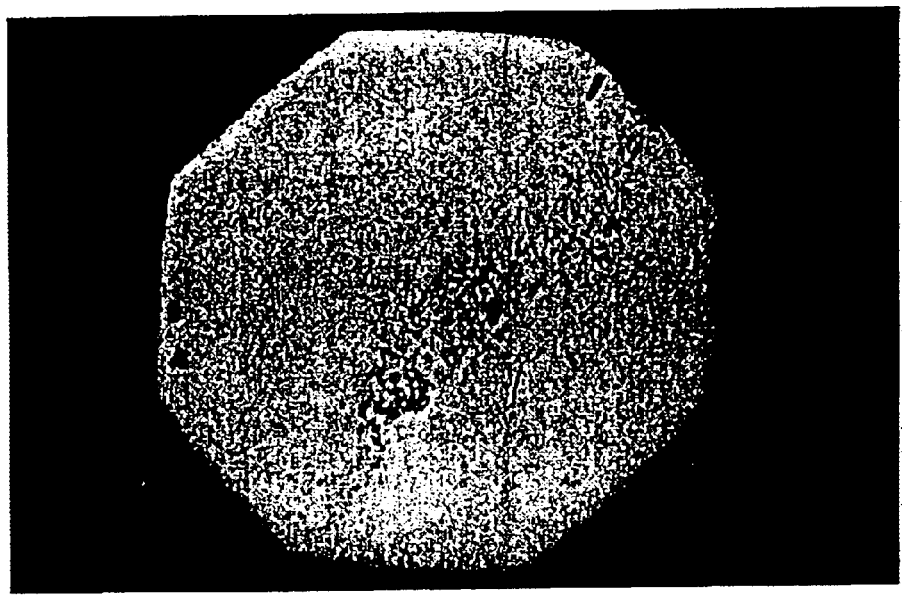
Figure 13:
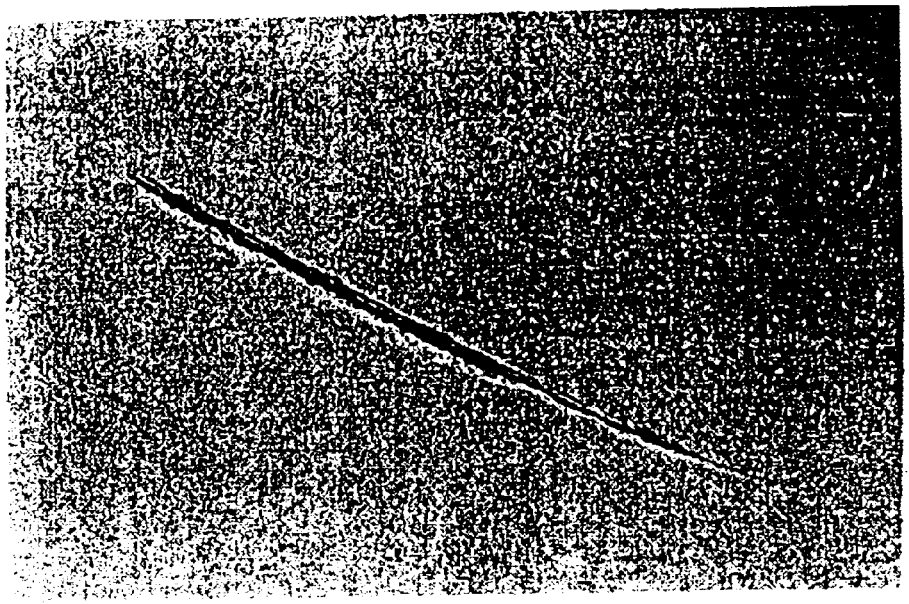
Figure 14:
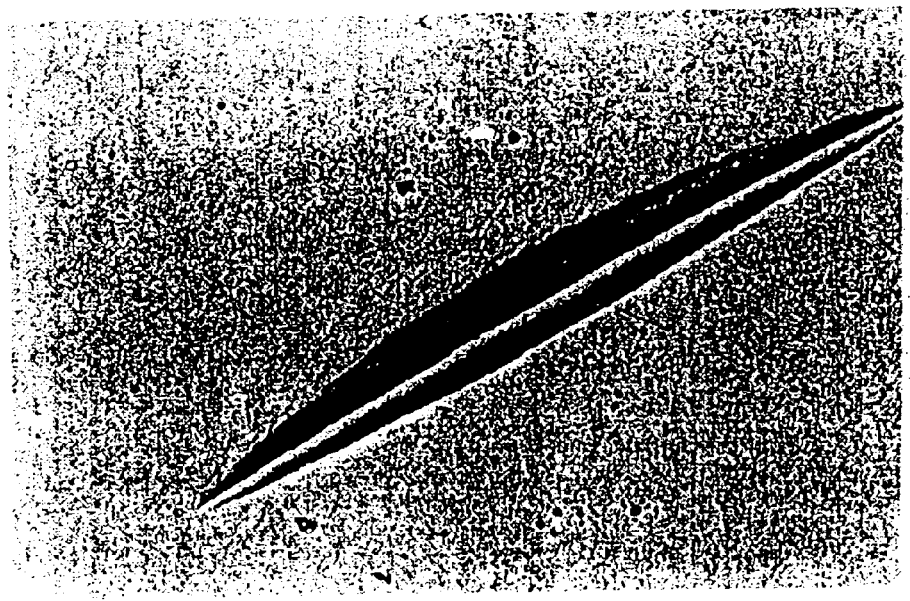

The pits shown in the in vivo used femoral ball of FIG. 7 and in the artificially aged femoral ball of FIG. 11 are believed due to the inclusion of second phase particles in the CoCrMo alloy used to manufacture the balls as discussed previously. Although scratches, gouges, and rough areas have previously been observed in CoCrMo femoral balls after in vivo use, these defects have been attributed to abrasive wear. However, as shown above, the same defects can be generated by long term aging in human synovial fluid without abrasive contact.

As explained in greater detail in Example 6, a comparison of the defects on in vivo used femoral balls as compared to defects developed during accelerated chemical aging, has shown that there was no statistical difference between the numbers and types of defects observed in the in vitro artificially aged, and the in vitro aged balls.

According to the second aspect of the invention, the larger, macro-defects such as scratches, gouges, and roughened areas depicted in FIGS. 7–10 and 11–15 are substantially minimized or eliminated. In accordance with this aspect of the invention, machine shaped articulating surfaces of cobalt-base alloy implants and implant components are prepared using precision cutting or metal removal operations which remove metal without deforming the metal alloy left on the surface of the implant or implant component.

Currently commercial available femoral balls are made by machining processes which involve grinding followed by a final surface polishing step. The conventionally used grinding and polishing steps deform the metal alloy sufficiently to form hidden or latent macrodefects which can be developed during use of the femoral balls. In accord with the present invention, these latent macro-defects are eliminated or minimized by using cutting operations which do not deform the metal alloy structure or provide a surface layer of deformed alloy.

In particular, precision metal cutting and metal removal processes and apparatus that can be used according to the invention include precision single point turning apparatus and operations, chemical machining operations, electro-chemical machining operations, laser beam machine operations, and electrochemical grinding operations such apparatus and operations being well known to the skilled artisan. In addition, multiple step grinding operations which are conducted insufficiently small incremental steps and using sufficiently sharp grinding media and conditions so that metal is removed and not deformed, can be employed according to this aspect of the invention. Although polishing as a final step may be used in order to remove burrs and the like, substantial conventional polishing is not preferred since it is believed that polishing deforms and moves the alloy structure sufficiently to provide a layer covering or containing defects in the surface of the precision machined component.

Figure 15:
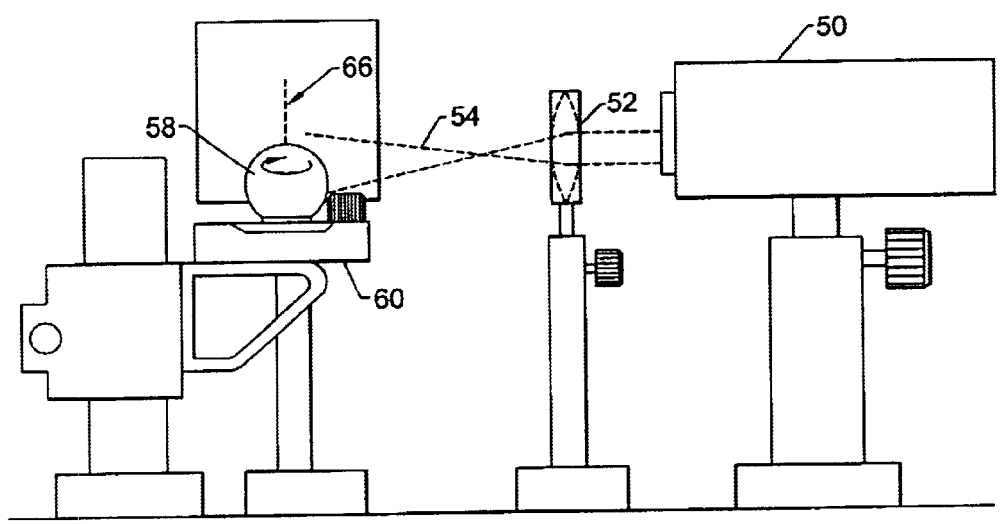
FIG. 15 schematically illustrates a precision laser inspection apparatus capable of identifying surface defects, of a size greater than 5 micrometers, on the articulating spherical surface of the ball components of joint implants.

Cutting operations may be evaluated to determine whether they avoid deforming the alloy structure sufficiently to avoid causing latent defects, according to this aspect of the invention, using the artificial aging technique described previously and detailed in Example 6. For evaluation, the precision machined implant articulating components, particularly articulating surfaces thereof, are subjected in a statistically significant number, preferably at least three samples, to the artificial aging test of Example 6. The articulating surfaces of the implant components are evaluated before and after the accelerated chemical aging using any precision inspection apparatus or procedure capable of identifying surface defects having at least one width or length dimension, i.e., at least one edge-to-edge dimension measurement, greater than 5 micrometers. Such inspection apparatus can include conventional profilometers, microscopes, laser inspection devices and the like. One particular laser inspection device is shown in FIG. 15 and discussed in greater detail in Example 6. In accord with the invention, no substantial increase in the number of defects of a size above 5 micrometers should be observed in surface inspection measurements taken before and after artificial aging. For articulating components made from CoCrMo alloys including second phase particles, a mean average increase in defects of greater than 10 is considered substantial. Preferably the mean average increase in defects is less than 7.5. In the case of CoCrMo articulating implant components in which the alloy is essentially free of second phase particles, an increase in defects above a mean average of 3.5 defects is considered substantial. Preferably, the mean average increase in defects is less than 2, more preferably less than 1.

EXAMPLE 1

This example illustrates production of single phase alloys of the invention as compared to prior art alloys. Fifty pounds of pure virgin raw materials commonly used to produce this alloy were weighed out to the aim composition (expressed in weight percent), G917-1 shown in Table A. The materials were processed in the usual manner. That is, they were placed in a vacuum furnace, melted and refined. Nominally 25-lbs. of this molten alloy was then cast in a metal mold and solidified. Additional virgin raw materials from the same lots were added to the remaining 25# of molten metal sufficient to adjust the chemical composition to G917-2 set forth in Table A. After this additional material was completely melted in, the alloy was held for a suitable refining period of approximately 30 minutes, and a second ingot was cast in the same manner.

These two ingots were removed from the vacuum furnace, heated side-by-side in a gas fired furnace to a temperature of 2150° F., then forged to 1"×1" square bars using identical practices.

Test samples were cut from these bars in the warm worked and air cooled condition for metalographic examination. There were striking differences in their micro-structure. FIGS. 1–4 show the typical structure at 1000× and 5000× for both materials as discussed previously. Heat G917-2 shows the large number of carbides and sigma phase particles typically seen in wrought bar of the CoCrMo alloy of ASTM 1537 (prior art). In contrast, Heat G917-1 shows a structure which is almost completely free of second phase particles.

TABLE A

|  | G917-1 | | G917-2 | | WB41 | |
| --- | --- | --- | --- | --- | --- | --- |
|  | Aim | Analysis | Aim | Analysis | Aim | Analysis |
| C | 0.050 | 0.53 | 0.050 | 0.52 | 0.010 | 0.009 |
| Mo | 5.50 | 5.36 | 6.75 | 6.64 | 5.25 | 5.15 |
| Cr | 26.50 | 26.32 | 28.50 | 27.19 | 26.50 | 26.24 |
| Ni | <0.06 | 0.60 | <0.60 | 0.61 | 0.75 | 0.69 |
| Co | Bal | 67.42 | Bal | 63.60 | Bal | 66.90 |
| Fe | LAP | 0.08 | LAP | 0.09 | LAP | 0.14 |
| Mn | LAP | 0.01 | 0.85 | 0.87 | 0.75 | 0.72 |
| Ti | <0.01 | 0.01 | <0.01 | 0.01 | <0.01 | 0.01 |
| Al | 0.10 | 0.09 | 0.10 | 0.06 | 0.10 | 0.08 |
| Si | LAP | 0.01 | 0.85 | 0.89 | LAP | 0.01 |
| $N_2$ | 0.185 | 0.129 | 0.185 | 0.142 | 0.180 | 0.118 |
| Ca | 0.04 | 0.004 | 0.04 | <0.001 | 0.04 | 0.004 |
| Cr + 1/2 Mo Co | | 0.43 | | 0.48 | | 0.43 |

EXAMPLE 2

To confirm the results of Example 1, another heat of CoCrMo alloy of the improved composition and essentially free of second phase particles, was produced (WB41) Table A. This time a slightly larger quantity (150#) of material was produced and the melting and hot working practices were closer to those used in current commercial production. Vacuum induction melting was used to produce a 4.25" diameter×150 lb electrode, which was vacuum arc remelted to a 5.50" diameter×150 lb ingot. The ingot was homogenized at 2200° F. and forged at a temperature in the range from 2150° F. to 2050° F., to an intermediate size, followed by hot rolling to 0.984" diameter bar at 2050° F. Metallographic examination of the hot rolled bar showed the microstructure of WB41 to be nearly identical to that of G917-1. That is, the bar stock from heat WB41, in the warm worked and air cooled condition was completely free of carbides and sigma phase particles in marked contrast to samples examined from commercial heats which contain numerous second phase particles.

EXAMPLE 3

Nitrogen is conventionally considered to be a strengthener for the CoCrMo alloy and is purposely added as an alloying element. Occasionally this results in the presence of large, blocky second phase particles in the alloy which have been identified as TiN. While titanium is not usually present in the alloy as a purposeful addition, it has been discovered that even very small traces will result in undesirable TiN particles. A series of samples were prepared by vacuum melting high purity virgin raw materials. Titanium content was purposefully varied from zero to 0.75 wt. % Ti while all other elements, including $N_2$, were held constant at levels which are typical for this alloy. Results illustrated that no nitrides were visible at 500× for titanium additions of 0.01 wt. %. However, with an addition of only 0.03 wt. %, large numbers of small titanium nitride particles were clearly visible in the microstructure and their size and quality grew as Ti content was further increased

EXAMPLE 4

To determine the wear characteristics of preferred alloys of this invention, a widely used experimental pin-on-disk test was performed in accordance with the American Society for Testing & Materials procedure ASTM F 732-82 (Reapproved 1991), "Reciprocating Pin-on-Flat Evaluation of Friction and Wear-Properties of Polymeric Materials Used in Total Joint Prostheses". In addition to the alloy of Example 2, samples were selected from a random commercial heat of CoCrMo bar (EF26) of about the same size and from a commercial heat of 316 stainless steel (ASTM F 138) as a reference standard. Flat disks (25 mm wide×100 mm long×6 mm thick) were prepared from all three metals and all were finished by polishing through 2000 grit paper to a mirror finish. Roughness measurements made with non-contact surface profilometry demonstrated that all samples were comparable to values observed for orthopaedic implants, and that there was no statistically significant difference between samples. Pins (9.5 mm diameter×19 mm long) were machined from Ultra High Molecular Weight Polyethylene (UHMWPE) bar produced in accordance with ASTM F 648 followed by gamma irradiation sterilization and pre-soaking in serum to a constant weight.

Testing was performed on a reciprocating bench under the following conditions (Table B):

TABLE B

| Experimental Conditions for Wear Testing | |
| --- | --- |
| Total Slide Distance | 150 km |
| Sliding Distance per Cycle | 0.01 m |
| Average Surface Velocity | 0.01 m/s |
| Contact Area | 71.25 $mm^2$ (0.11 $in^2$) |
| Metal Counterface Finish (RMS) | 0.002–0.006 $\mu m$ |
| Lubricant | Blood Bovine Serum + 0.2% Sodium Azide + 20 mM Ethylene Diamine Tetraacetate (EDTA) |

A series of six test coupons were run-from each of the CoCrMo samples and three from the 316SS reference material. Results are shown in the following Table C:

TABLE C

Wear Parameters of Ultra High Molecular Weight Polyethylene vs. Test Alloys

| Average Steady State Wear Calculations | UHMWPE vs. CoCrMo - EF26 (Commercial Alloy) | UHMWPE vs. CoCrMo - WB41 (Alloy of the Present Invention) | UHMWPE vs. 316L SS (Reference Standard) |
| --- | --- | --- | --- |
| Calculated Wear Rate ($mg/10^6$) | 0.1167 ± 0.0104 | 0.0692 ± 0.0063 | 0.1800 ± 0.1040 |
| Corrected* Wear Rate ($mg/10^6$) | 0.1297 ± 0.0104 | 0.0822 ± 0.0063 | 0.1997 ± 0.1040 |
| Volume Loss (p = 0.93,$mm^3$/$10^6$) | 0.1395 ± 0.112 | 0.0884 ± 0.095 | 0.1516 ± 0.0323 |
| Height Loss ($\mu m/10^6$) | 1.958 ± 0.157 | 1.241 ± 0.095 | 2.127 ± 0.454 |
| Wear Factor (($mm^3$/(Nm)*$10^{-7}$) | 0.7990 ± 0.0641 | 0.5064 ± 0.0388 | 0.8683 ± 0.1851 |

*Weight changes measured in loaded control tests were used to correct for creep during testing according to Dowson, et al. "Wear," 190:171–183, (1995).

These data show a substantial and statistically significant reduction in the wear rate of the UHMWPE when rubbing against the alloy of this invention (WB41) as compared to the standard commercial CoCrMo alloy (EF26) and the reference 316SS.

EXAMPLE 5

To determine the fatigue properties of the alloy prepared in Example 2, test samples were machined from bar in the warm rolled and air cooled condition and tested in accordance with standard specifications MIL-145206, Rev. A, Amendment 1 (24 Jul. 8) and MIL-STD45662, Rev. A.

As a basis of comparison, samples were likewise machined from bar samples in the same condition from a standard commercial heat of Co-Cr-Mo Alloy ASTM 1537 (Prior Art). Both materials were produced in essentially the identical manner.

Since fatigue life for metals is directly proportional to yield strength, tensile tests were performed from both lots of materials with the results presented in Table D. From these data, it is apparent that tensile properties, particularly yield strength for these two lots of material, are quite close, with the standard commercial material having a slightly higher 0.2% yield strength (135 Ksi vs. 130 Ksi).

Fatigue life of metals can also be influenced by grain size. Grain size measurements of these two test lots, also presented in Table D, show identical results within the limits of the measurement method.

Fatigue test results for the alloy of this invention and the standard commercial alloy are summarized in Table E. These results show a significant improvement in the Fatigue Endurance Limit Fatigue Life), defined as the stress to produce a life on 10,000,000 cycles, for the Alloy of the Present Invention compared to the Standard Commercial Alloy. The endurance limit for WB41 (Alloy of the Present Invention) was conservatively 125 Ksi and very near 130 Ksi. This compares to an Endurance limit for JK60 (the Standard Commercial Alloy) of between 110–115 Ksi. This result for the Standard Commercial Alloy is just over 81% of the yield strength, which is very close to the 80% value considered typical for many metals. By comparison, this ratio is greater than 96% for the Alloy of the Present Invention. Remarkably, the Fatigue Endurance Limit for the Alloy of the Present Invention is almost the same as the yield strength of the alloy.

TABLE D

Room Temperature Tensile Properties**

| | UTS Ksi | .2% YS Ksi | % EI | % RA | HRC | ***Grain Size |
|---|---|---|---|---|---|---|
| *Heat WB41 (Alloy of the Present Invention) | 192 | 130 | 30 | 25 | 41 | ASTM 10-12 |
| | 188 | 129 | 25 | 21 | | |
| | 194 | 131 | 19 | 24 | | |
| Heat JK60 Commercial Alloy) | 187 | 136 | 22 | 20 | 40 | ASTM 10-12 |
| | 187 | 135 | 23 | 21 | | |

*Specimens taken from 0.937 diameter bar in the as-rolled condition.
**Tensile tests performed according to ASTM E 8, hardness tests according to ASTM E 18.
***Grain size measurements to ASTM E 112, comparison method.

TABLE E

Smooth Rotating Beam Fatigue Test Results*

| | Sample No. | Applied Stress (Ksi) | Total Cycles | Fatigue Locations |
|---|---|---|---|---|
| Heat No. WB41 (Alloy of Present Invention) | 1 | 105 | 10,000,000 | Unloaded |
| | | 135 | 4,905,640 | Gage |
| | 2 | 115 | 10,000,000 | Discontinued |
| | 3 | 125 | 10,000,000 | Discontinued |
| | 4 | 135 | 9,196,872 | Gage |
| | 5 | 130 | 10,000,000 | Discontinued |
| | 6 | 130 | 9,289,000 | Gage |

TABLE E-continued

Smooth Rotating Beam Fatigue Test Results*

| | Sample No. | Applied Stress (Ksi) | Total Cycles | Fatigue Locations |
|---|---|---|---|---|
| JK60 (Standard Commercial Alloy) | 1 | 105 | 10,000,000 | Discontinued |
| | 2 | 115 | 6,507,000 | Gage |
| | 3 | 110 | 15,377,000 | Gage |
| | 4 | 110 | 10,000,000 | Discontinued |
| | 5 | 115 | 10,000,000 | Discontinued |

*0.200" Diameter Samples, Low Stress Grind, Room Temperature Tests in Air, Fully Reversed Bending (R = −1).

EXAMPLE 6

This example illustrates accelerated aging of CoCrMo femoral balls.

Fifteen commercially available CoCrMo femoral implant balls were obtained from five manufacturers (three balls from each manufacture). The balls were artificially aged according to an accelerating aging test by immersing the balls in human synovial fluid inside a sealed aluminum pressure vessel and heating the pressure vessel to a temperature of 159° C. plus or minus 1° C., for 8.6 days. The vessels were sealed by Teflon gaskets in order to prevent the escape of vapor during the heating. It was estimated that a pressure of about 250 psi existed during the tests.

The test was designed to simulate 12 years of chemical interaction at body temperature based on the Arrhenius equation:

$$R = Ae^{-E/kt},$$

where R is the chemical reaction rate, A is a constant, E is the activation energy of the reaction, k is Boltzrnann's constant, and T is the Kelvin temperature of the reaction. Increasing the temperature will increase the reaction rate as follows:

$$mR = Ae^{E/k(T+\Delta T)}$$

where m is the multiplication factor and $\Delta T$ is the rise in the temperature. If $\Delta T$ is small compared to T, then:

$$\Delta T = kT^2 \ln(m)/E.$$

For a doubled reaction rate, m is 2, E is taken to be 0.6 electron volts (which is a value near many chemical reactions), and T is 310.15° K. (human body temperature), which gives a $\Delta T$ of 10° K. To replicate the in vivo aging of 12 years over a relatively short test time it is necessary to increase the in vitro reaction rate by a factor of several hundred. Since the equation is non-linear with respect to temperature, and valid only for small values of $\Delta T$, the equation was applied in nine sequential steps. The nine steps included the first step which started at an initial T of 310.15° K., (body temperature), to find the value of $\Delta T$, which was then used to calculate T for the next step, and so on. In this manner it was determined that a temperature of 159° C. should increase reaction rate by a factor of $2^9$, i.e., 512, as compared to body temperature. Thus, 8.6 days at 159° C. should produce a chemical interaction between the joint synovial fluid and the ball surface generally corresponding to an in vivo chemical interaction period of 12 years.

The artificially aged balls were removed from the test fluid and then examined for defects using the apparatus shown in FIG. 15. With reference to FIG. 15, collimated laser light at 632.8 nm wavelength is supplied from laser 50 to a converging lens 52 which focuses the light and causes the laser beam 54 to diverge. The divergent light was directed to the surface of a test femoral ball 58 which rested upon a small rotatable table 60. The laser light hitting the ball was reflected from the ball onto a curved screen which was concentric with the center of the ball. The portion of the reflected light reflected away from the screen was blocked by a card (not shown) to protect the eyes of the observers. As the ball was rotated, macroscopic defects appeared on the screen as dark features which were magnified by a factor of 4. These dark features, usually surrounded by an optical diffraction pattern, moved across the screen as the ball was rotated and could be counted as they crossed a line 66, on the screen as the ball was rotated through one revolution. This gave the number of defects on the ball above a size of about 5 micrometers.

Two groups of femoral balls were analyzed. Three virgin femoral balls were supplied by each of five orthopedic manufacturers and subjected to accelerated aging as discussed above. A control group of five harvested balls were obtained during revision of failed conventional total hip arthroplasties (metal to plastic articulation). Each ball in the control harvested group had at least ten years of in vivo service life prior to revision.

The results of analyzing surface defects on both groups of balls are shown in Tables F and G below, in which Table F shows the total number of defects for each ball, while Table G shows the average number of defects of each type for the groups of balls tested.

TABLE F

| Virgin Balls Sample No. | Damage | Harvested Balls Sample No. | Damage |
| --- | --- | --- | --- |
| 1-1 | 8 | H-1 | 13 |
| 1-2 | 10 | H-2 | 20 |
| 1-3 | 8 | H-3 | 15 |
| 2-1 | 13 | H-4 | 15 |
| 2-2 | 10 | H-5(S.S.) | High damage |
| 2-3 | 20 | H-6(S.S.) | High damage |
| 3-1 | 17 | H-7 | 13 |
| 3-2 | 11 | H-8 | 17 |
| 3-3 | 9 | H-9 | 16 |
| 4-1 | 11 | H-10 | 13 |
| 4-2 | 12 | H-11 | 7 |
| 4-3 | 19 | H-12 | 17 |
| 44-1 | 13 | H-13 | 13 |
| 44-2 | 16 | H-14 | 11 |
| 44-3 | 9 | H-15 | 11 |
| Average degradation | 12.4 | | 13.9 |
| Standard deviation | 3.91 | | 3.3 |
| One standard error | 1.01 | | 0.916 |

TABLE G

| Group | Virgin Balls | Harvested Balls |
| --- | --- | --- |
| Pits | 8.58 | 7.07 |
| Scratches | 2.0 | 1.46 |
| Gouge | 1.46 | 3.76 |
| Rough Patch | 1.53 | 1.75 |

Note: This table shows the average values per sample for each kind of defect.

While particular embodiments of the invention have been described, it will be understood, of course, that the invention is not limited thereto since modifications may be made by those skilled in the art, particularly in light of the foregoing teachings. It is therefore, contemplated by the appended claims to cover any such modifications that incorporate those features of these improvements in the true spirit and scope of the invention.

What is claimed is:

1. A biocompatible cobalt-base alloy comprising chromium and molybdenum, said alloy being essentially free of carbide, nitride, and sigma second phase particles, wherein said alloy has a yield strength greater than about 120 Ksi and a grain size finer than about ASTM 10.

2. The biocompatible cobalt-base alloy of claim 1, said alloy being essentially free of any second phase particles.

3. The biocompatible cobalt-base alloy of claim 1 wherein said alloy is a forged alloy.

4. The biocompatible metal alloy of claim 3, wherein said alloy has a hardness greater than about 40 $R_c$.

5. The biocompatible metal alloy of claim 1, wherein said alloy consists essentially of:

from about 26 to about 28 weight percent chromium;

from about 5 to 6 weight percent molybdenum;

up to about 1 weight percent manganese;

up to about 1 weight percent nickel, up to about 0.75 weight percent iron;

up to about 0.07 weight percent carbon;

nitrogen in an amount up to about 0.25 weight percent:

less than about 0.100% Si;

less than about 0.02% Ti, the remainder of the alloy being cobalt and impurities.

6. A biocompatible cobalt-base alloy of claim 1 wherein said alloy has a ratio of (weight percent Cr+½ weight percent Mo)/weigh percent Co in the range of below about 0.450.

* * * * *

UNITED STATES PATENT AND TRADEMARK OFFICE
CERTIFICATE OF CORRECTION

PATENT NO.    : 6,773,520 B1
DATED         : August 10, 2004
INVENTOR(S)   : Fehring et al.

It is certified that error appears in the above-identified patent and that said Letters Patent is hereby corrected as shown below:

<u>Column 18,</u>
Line 43, "0.100%" should read -- 0.10% --.

Signed and Sealed this

Thirtieth Day of November, 2004

JON W. DUDAS
*Director of the United States Patent and Trademark Office*